United States Patent
Seo (10) Patent No.: US 9,993,136 B2
(45) Date of Patent: Jun. 12, 2018

(54) ENDOSCOPY INSTRUMENT GUIDE PORT

(75) Inventor: O-Nam Seo, Bucheon-si (KR)

(73) Assignee: O-Nam Seo, Gyeonggi-do (KR)

(*) Notice: Subject to any disclaimer, the term of this patent is extended or adjusted under 35 U.S.C. 154(b) by 683 days.

(21) Appl. No.: 13/817,841

(22) PCT Filed: Sep. 8, 2011

(86) PCT No.: PCT/KR2011/006645
§ 371 (c)(1),
(2), (4) Date: Feb. 20, 2013

(87) PCT Pub. No.: WO2012/033358
PCT Pub. Date: Mar. 15, 2012

(65) Prior Publication Data
US 2013/0158354 A1    Jun. 20, 2013

(30) Foreign Application Priority Data

Sep. 10, 2010  (KR) .................. 10-2010-0088656
Oct. 13, 2010  (KR) .................. 10-2010-0099563

(51) Int. Cl.
*A61B 17/02*    (2006.01)
*A61B 1/00*     (2006.01)
(Continued)

(52) U.S. Cl.
CPC ...... *A61B 1/00131* (2013.01); *A61B 17/0293* (2013.01); *A61B 17/3423* (2013.01); *A61M 39/06* (2013.01); *A61B 2017/3466* (2013.01)

(58) Field of Classification Search
CPC ............ A61B 17/0293; A61B 17/3431; A61B 17/3462; A61B 17/3498;
(Continued)

(56) References Cited

U.S. PATENT DOCUMENTS 6,254,533 B1   7/2001  Fadem et al.
8,986,202 B2*  3/2015  Butler et al. .................. 600/208
(Continued)

FOREIGN PATENT DOCUMENTS

KR    10-0936926 B1    1/2010

OTHER PUBLICATIONS

International Search Report for PCT/KR2011/006645.

*Primary Examiner* — Timothy J Neal
(74) *Attorney, Agent, or Firm* — The PL Law Group, PLLC (57) ABSTRACT

An endoscopy instrument guider port includes a main body member where at least one surgical instrument entrance part is disposed at an upper surface, a protective tube extending downwards from the main body member, a retaining ring body fixed to a lower end portion of the protective tube, the retaining ring body being freely deformed and restored, and a control ring body disposed at a predetermined position along a length direction of the protective tube to be coiled around the protective tube through a folding motion and control a length of the protective tube. According to the present invention, the control ring body disposed at the protective tube facilitates length adjustment and traction generation of the protective tube, appropriate handling of surgical situations is possible because an upper body may be turned and separated, and surgical delays may be prevented while endoscopy operations may be made easier.

6 Claims, 11 Drawing Sheets

(51) Int. Cl.
  *A61B 17/34*   (2006.01)
  *A61M 39/06*   (2006.01)

(58) Field of Classification Search
  CPC ........ A61B 2017/3445; A61B 1/00131; A61B 17/3423; A61B 2017/3466; A61B 1/00135; A61B 1/00154; A61M 39/03
  USPC .................. 600/114, 201, 207, 137; 604/308
  See application file for complete search history.

(56) References Cited

U.S. PATENT DOCUMENTS

| | | | |
|---|---|---|---|
| 2005/0020884 A1* | 1/2005 | Hart | A61B 17/0293 600/206 |
| 2009/0036745 A1* | 2/2009 | Bonadio et al. | 600/208 |
| 2009/0082632 A1* | 3/2009 | Voegele | A61B 17/3423 600/204 |
| 2010/0204548 A1 | 8/2010 | Bonadio et al. | |
| 2010/0231972 A1* | 9/2010 | Tokimatsu | H04N 1/32523 358/1.15 |
| 2010/0249694 A1 | 9/2010 | Choi et al. | |

* cited by examiner

ENDOSCOPY INSTRUMENT GUIDE PORT

CROSS REFERENCE TO RELATED APPLICATIONS AND CLAIM OF PRIORITY

This patent application claims benefit under 35 U.S.C. 119(e), 120, 121, or 365(c), and is a National Stage entry from International Application No. PCT/KR2011/006645, filed Sep. 8, 2011, which claims priority to Korean Patent Application numbers 10-2010-0088656 filed Sep. 10, 2010, and 10-2010-0099563 filed Oct. 13, 2010, entire contents of which are incorporated herein by reference.

BACKGROUND

1. Technical Field

The present invention relates to an endoscopy instrument guide port.

2. Description of the Related Art

In general, since a size of an operation hole (incision window) of a laparoscopic endoscopic operation (that is also called 'minimally invasive surgery') is small as compared with that of a traditional laparotomy operation, the laparoscopic endoscopic operation has merits that scars left from surgery are not bad-looking, pain due to the wound is more reduced, and the hospital treatment period is shorten due to a short recovery time so that the patient returns more quickly to daily life. Thus, in recent years, the laparoscopic endoscopic operation has been widely conducted for most diseases except for several cancers.

According to the endoscopic operation, a small hole is perforated in the belly of a patient by using an intubation surgical device called a trocar, in which at least one trocar is inserted into the belly and various surgical devices such as a forceps, a cutting device, an internal organ extraction device, and an endoscopic camera are introduced to an operated portion in the belly through the trocar to perform various operations such as cholecystectomy, biliary stone removal, appendectomy, and a general surgical operation.

Meanwhile, in recent years, endoscopic operations are being performed through a portion of a navel by using a plurality of trocars described above without incising the belly to reduce the scar left in the belly of the patient and allow the patient to recover promptly.

In general, if a hole for an operation is perforated in the navel of a human body, the scar is not easily exposed to the outside even after the wound is healed up and is not visually recognized as the scar, so an endoscopic operation through a navel is currently preferred.

In order to perform such a surgical operation, an operation hole of 10 mm to 12 mm is perforated in the navel according to the type of the operations, and a surgical tool guide for introducing various surgical tools into the belly is installed in the operation hole to be used.

However, the surgical tool guide according to the related art delays an operation because the surgical tool guide is easily separated from its installation position such as a belly or nitrogen gas introduced to ensure the operation space is often leaked during the operation. In this regard, the present applicant has developed a surgical tool guide for preventing separation of the guide to ensure a smooth operation, which was filed on Mar. 27, 2009 and registered as Korean Patent No. 10-915882.

Figure 13:
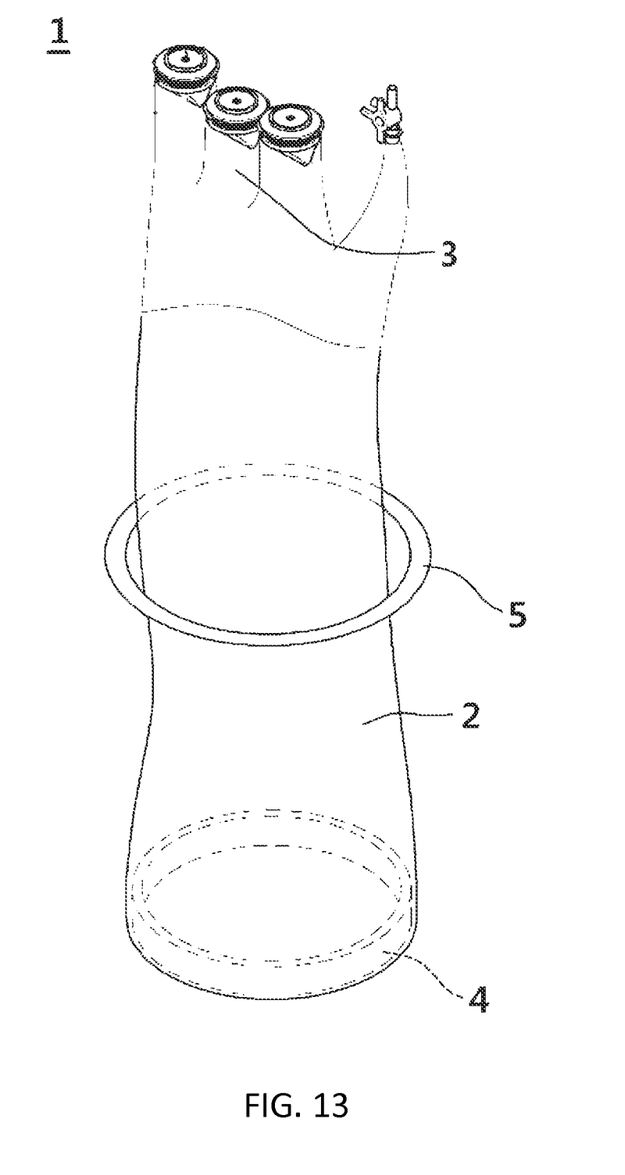
FIGS. 13 and 14 are views illustrating a configuration and an operation of an endoscopic instrument guide port according to the related art.

The patented surgical tool guide of Korean Patent No. 10-915882 is shown in FIG. 13. In the surgical tool guide 1, a plurality of tool entrances 3 for entry of various surgical tools are provided at an upper portion of a body 2, an attaching ring 4 having a resiliency to be attached to and supported by an upper portion of an operation hole is installed at an end of an opened bottom surface of the body 2, and a support ring 5 is located at an outer portion of the body 2 in the longitudinal direction of the body 2 in an interior, which is defined as the attachment ring 4 overlaps an outer wall of the body 2, in order to support the body 2 in correspondence with the attachment ring 4 according to a thickness of an abdominal wall when it is introduced into an abdominal cavity through an operation hole.

Figure 14:
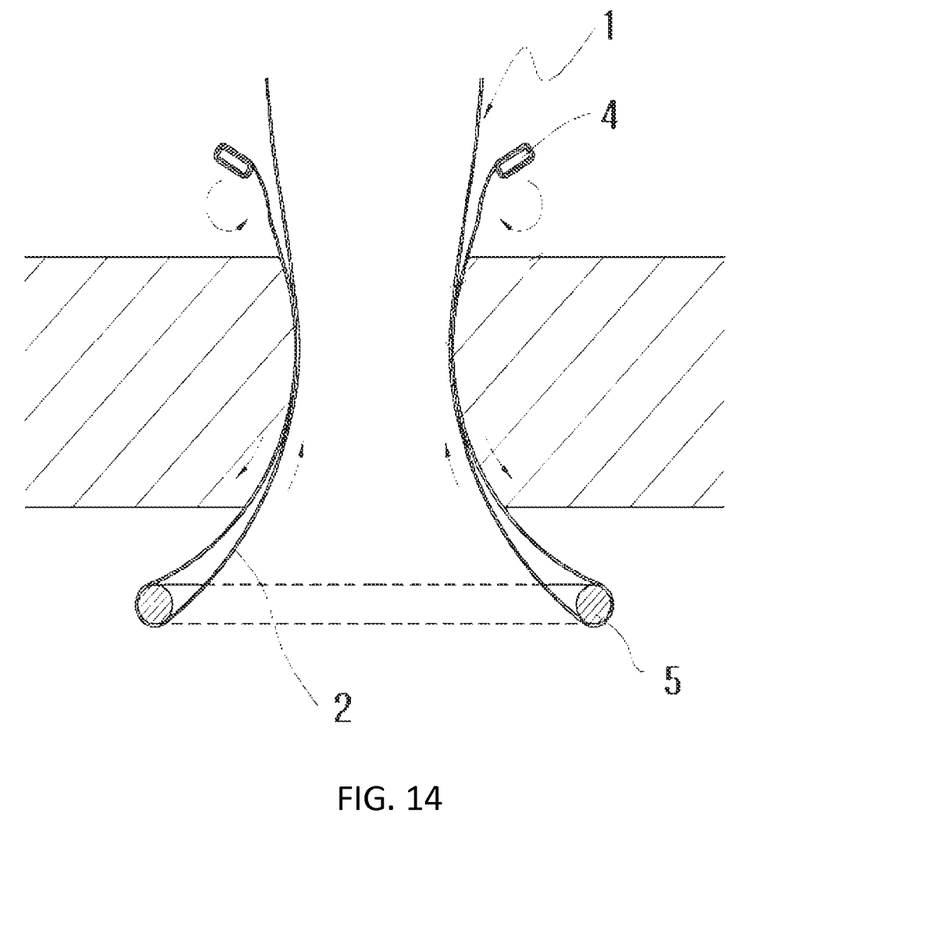

According to the surgical tool guide 1 as shown in FIG. 14, the attaching ring 4 located at an upper portion of the operation hole is folded upward in a state that the support ring 5 is suspended in the abdominal cavity such that the attachment ring 4 can be positioned at an upper side of the belly according to a thickness of the belly wall to tightly tension the body 2. Thus, the surgical tool guide 1 is not easily separated from the operation hole during the operation and the body 2 can be tightly maintained between the support ring 5 and the attaching ring 4.

However, in spite of the merits described above, there are several problems in the above surgical tool guide. First, since the attaching ring 4 is provided at an end portion of the body 2 after the body 2 has surrounded the support ring 5, even if the attaching ring 4 is wrapped in the state that the support ring 5 is suspended in the abdominal cavity, only a portion of the body 2 between the support ring 5 and the attachment ring 4 is tightly tensioned and a portion of the body 2 extending toward the surgical instrument entrance parts 3 from the support ring 5 may not be sufficiently tensioned.

Thus, it is difficult to properly adjust the length of the body 2 in the state that the support ring 5 is introduced in the abdominal cavity through the operation hole. Therefore, when the installed body 2 is too long (that is, the length from the operation hole to the surgical instrument entrance part is too long), there is a problem to reintroduce the support ring 5 into the abdominal cavity after adjusting the length of the body 2 by taking the introduced support ring 5 out of the abdominal cavity. Further, since the traction force for expanding the operation hole is insufficient, it is limited to ensure the space and the visual field for entry of a surgical instrument so that the operation may not be smoothly performed.

Further, since the surgical instrument entrance parts 3 are integrally and fixedly formed with the body 2, the positions of surgical instruments may not be changed after the surgical instruments are introduced into the abdominal cavity, so that the positions of the surgical instruments may not be properly adjusted according situations during the operation. Thus, when it is necessary to control the positions of the surgical instruments, after the surgical instruments are inevitably taken out of abdominal cavity to change the positions of the surgical instruments, the surgical instruments must be again introduced inconveniently in the abdominal cavity through the surgical instrument entrance part.

In addition, when an organic extraction of a large size is resected during the operation after installation of the surgical tool guide, it is impossible to take the organic extraction out of the belly if the installed surgical tool guide is not dismantled. Further, since the distance between the surgical instrument entrance parts 3, through which the surgical instrument is introduced, and the belly is too long, the operation is difficult and the distance control is not easy.

SUMMARY

The present invention has been made in an effort to solve one or more of the above-described problems, and an aspect of the present invention is to provide an endoscopy instrument guide port which can easily and simply control a length of a protective tube in an installed state thereof and can ensure the traction force for expanding an operation hole.

An embodiment of the present invention also provides an endoscopy instrument guide port in which a surgical instrument entrance part is constructed to be rotated in a horizontal direction and to be separated as necessary such that the surgical instrument entrance part can be properly modified according to the operation situation.

An embodiment of the present invention also provides an endoscopy instrument guide port in which an upper tube is connected to or separated from a lower tube through a tube connection unit such that the upper tube can be separated if necessary, such as for organic extraction, and the length of the guide can be easily adjusted according to the conditions of the patient and the operation environment so that an operation can be smoothly performed.

In order to solve the above problems, according to an aspect of the present invention, there is provided an endoscopy instrument guide port including a main body member having a top end at which at least one surgical instrument entrance part is formed; a protective tube extending downward from the main body member by a predetermined length; a support ring member provided at a lower end portion of the protective tube, the support ring member being freely deformed and restored; and an adjustment ring member fixedly provided at a predetermined position lengthwise along the protective tube to coil the protective tube through a folding motion in order to adjust a length of the protective tube.

The main body member includes an upper cap having a top end at which at least one surgical instrument entrance part is formed; and a rail ring member connected to the protective tube to support the upper cap such that the upper cap is able to horizontally rotate.

Further, there is provided an endoscopy instrument guide port including an upper cap having a top end at which at least one surgical instrument entrance part is formed; a rail ring member supporting the upper cap such that the upper cap is able to rotate in a horizontal direction; a protective tube connected to the rail ring member and extending downward by a predetermined length; and a support ring member provided at a lower end portion of the protective tube, the support ring member being freely deformed and restored.

The coupling ring member is formed at an upper end portion of the protective tube, a coupling member coupled to the coupling ring member is formed at a lower end portion of the rail ring member, and the rail ring member and the protective tube are detachably connected to each other.

The rail space portion is formed inside the rail ring member, and a shaft end protrudes from a lower end of the upper cap and is received in the rail space portion such that the shaft end is slidably rotated in a horizontal direction.

In addition, the endoscopy instrument guide port further includes a packing ring member received in the rail space portion and disposed above and below the shaft end in the rail space portion.

In addition, there is provided an endoscopy instrument guide port including an upper tube having a top end portion at which at least one surgical instrument entrance part is formed; a lower tube having a lower end portion at which a support ring freely deformed and restored is provided; and a tube connection unit for detachably coupling the upper tube and the lower tube.

The tube connection unit includes an upper ring member fixed to a lower end portion of the upper tube; and a lower ring member fixed to an upper end portion of the lower tube, and, in a state that the upper ring member is fitted around the lower ring member, the lower ring member is folded outward to coil the upper and lower tubes together such that the upper and lower tubes are connected to each other.

The lower ring member has a longitudinal length longer than a longitudinal length of the upper ring member.

The endoscopy instrument guide port according to the present invention can easily and simply control the length of the protective tube in an installed state thereof through a folding operation of the adjustment ring member included in the protective tube and tightly tension the protective tube through the length adjustment, so that a sufficient traction force can be ensured.

Further, since the surgical instrument entrance part can be rotated in a horizontal direction, a suitable treatment can be performed by rotating the upper cap without taking a surgical instrument out of the belly when necessary to adjust a position of the surgical instrument during an operation.

In addition, an organic extraction can be taken out of a belly by separating only the upper tube without a need to disassemble the entire endoscopy instrument guide port when it is necessary to take the organic extraction out of the belly. Specifically, after separating the upper tube, if the lower ring member is continuously coiled, the operation hole is expanded so that an organic extraction having a large size can be very easily extracted.

Further, in the state that the upper tube and the lower tube are connected to each other, the length of the guide can be easily adjusted through the coiling operation of the lower ring member and in addition, the extension of the operation hole can be smoothly controlled so that the operation can be more easily performed.

In addition, if the lower tube is used after separating the upper tube from the lower tube, the lower tube can be utilized as a wound protector to protect an incised surface of an operation hole.

Furthermore, besides the above effects, the unique effects, which can be easily induced and expected from the feature and configurations of the present invention, are also included in the effects of the present invention.

DETAILED DESCRIPTION

Hereinafter, an exemplary embodiment of an endoscopy instrument guide port according to the present invention will be described in detail with reference to the accompanying drawings.

The embodiment is provided to more fully describe the present invention to those skilled in the art to which the present invention pertains, and it is noted that the shapes and sizes of elements in the drawings may be exaggerated to emphasize a more clear description.

Further, in the description of the embodiment, a detailed description of known functions and configurations which are apparent to those skilled in the art to which the present invention pertains will be omitted when they may make the technical feature of the present invention unnecessarily unclear.

FIGS. 1 to 4 are drawings showing an endoscopic instrument guide port 100 according to the first embodiment of the present invention. Referring to the drawings, an endoscopic instrument guide port (hereinafter, referred also to as 'surgical instrument guide port') 100 according to the first embodiment of the present invention includes a main body member 110, a protective tube 120, and a support ring member 130.

First, the main body member 110 has a top end at which at least one surgical instrument entrance part 110a is formed. Here, the surgical instrument entrance part 110a is provided for the purpose of introducing various surgical instruments such as forceps or an endoscope into the surgical instrument guide port 100 for a laparoscopic operation. A valve unit 110b may be provided at an upper end portion of the surgical instrument entrance part 110a for the purpose of easily introducing the surgical instrument with preventing gas leakage as possible.

Since various configurations of the surgical instrument entrance part 110a are well known in the art, the detailed description thereof will be omitted. In addition, it is possible to construct the surgical instrument entrance part 110a according to an embodiment of the present invention in various configurations, so configurations of the surgical instrument entrance part 110a are not limited to those shown in the drawings.

Further, in addition to the surgical instrument entrance part 110a, a gas adjusting valve 110c may be provided at an upper portion of the main body member 110 for the purpose of controlling entry and exit of the gas for expanding a belly.

The protective tube 120 has a hollow shape and extends downward from the main body member 110 by a predetermined length. The protective tube 120 may be formed of a urethane sheet having an excellent resiliency and durability.

The support ring member 130 which is a ring having an annular shape is fixed to a lower end portion of the protective tube 120.

When the surgical instrument guide port 100 is installed, the support ring member 130 is suspended to an abdominal wall in an abdominal cavity after passing through an operation hole of a patient so that the support ring member 130 performs a function of supporting the surgical instrument guide port 100. Thus, the support ring member 130 is formed of a resilient material which can be freely deformed, that is, can be folded or shrunk to be easily suspended during and after passing through the operation hole, and can be directly restored into an original state if an external force is removed.

The surgical instrument guide port 100 according to the first embodiment of the present invention having the configuration described above may further include an adjustment ring member 140.

The adjustment ring member 140, which is used for controlling a length of the protective tube 120, may be fixed at a predetermined position lengthwise along the protective tube 120. Preferably, the adjustment ring member 140 is substantially provided at a middle portion between the main body member 110 and the support ring member 130.

Further, the adjustment ring member 140, which has a ring shape, may be attached and fixed to an inner side surface or an outer side surface of the protective tube 120. A sectional surface of the adjustment ring member 140 may substantially have a rectangular shape.

Figure 4:
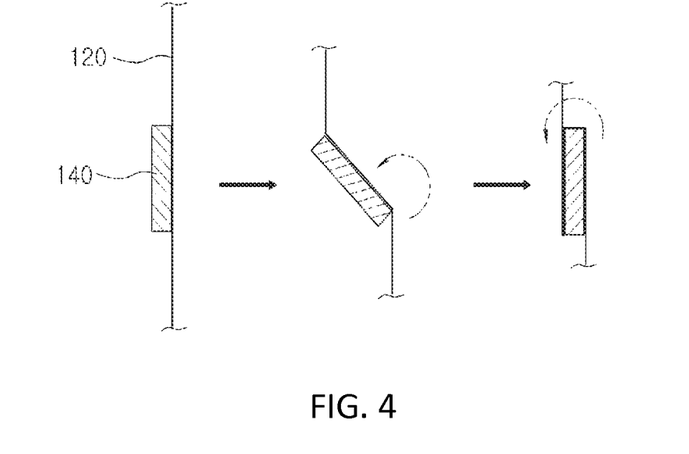
FIG. 4 is a sectional view illustrating an operation of an adjustment ring member according to the first embodiment of the present invention.

The adjustment ring member 140 coils the protective tube 120 through a folding operation so that the length of the protective tube 120 can be adjusted. As shown in FIG. 4, if the adjustment ring member 140 fixed to the protective tube 120 is folded, the protective tube 120 is coiled around the adjustment ring member 140 while the protective tube 120 is being folded, so that the length of the protective tube 120 is reduced by the extent that the protective tube 120 is folded. Thus, the length of the protective tube 120 may be easily controlled and traction force may be obtained by controlling the number of folding times of the adjustment ring member 140.

That is, if the protective tube 120 is continuously coiled around the adjustment ring member 140, the length of the protective tube 120 is reduced more and more. Thus, the distance between the surgical instrument entrance part 110 of the main body member 110 and the belly may be reduced and in addition, the protective tube 120 is tightly strained, so that great traction force, by which an operation hole is expanded, may be generated.

Further, the surgical instrument guide port 100 according to the first embodiment of the present invention may be implemented such that the main body member 110 is able to be rotated horizontally.

Figure 1:
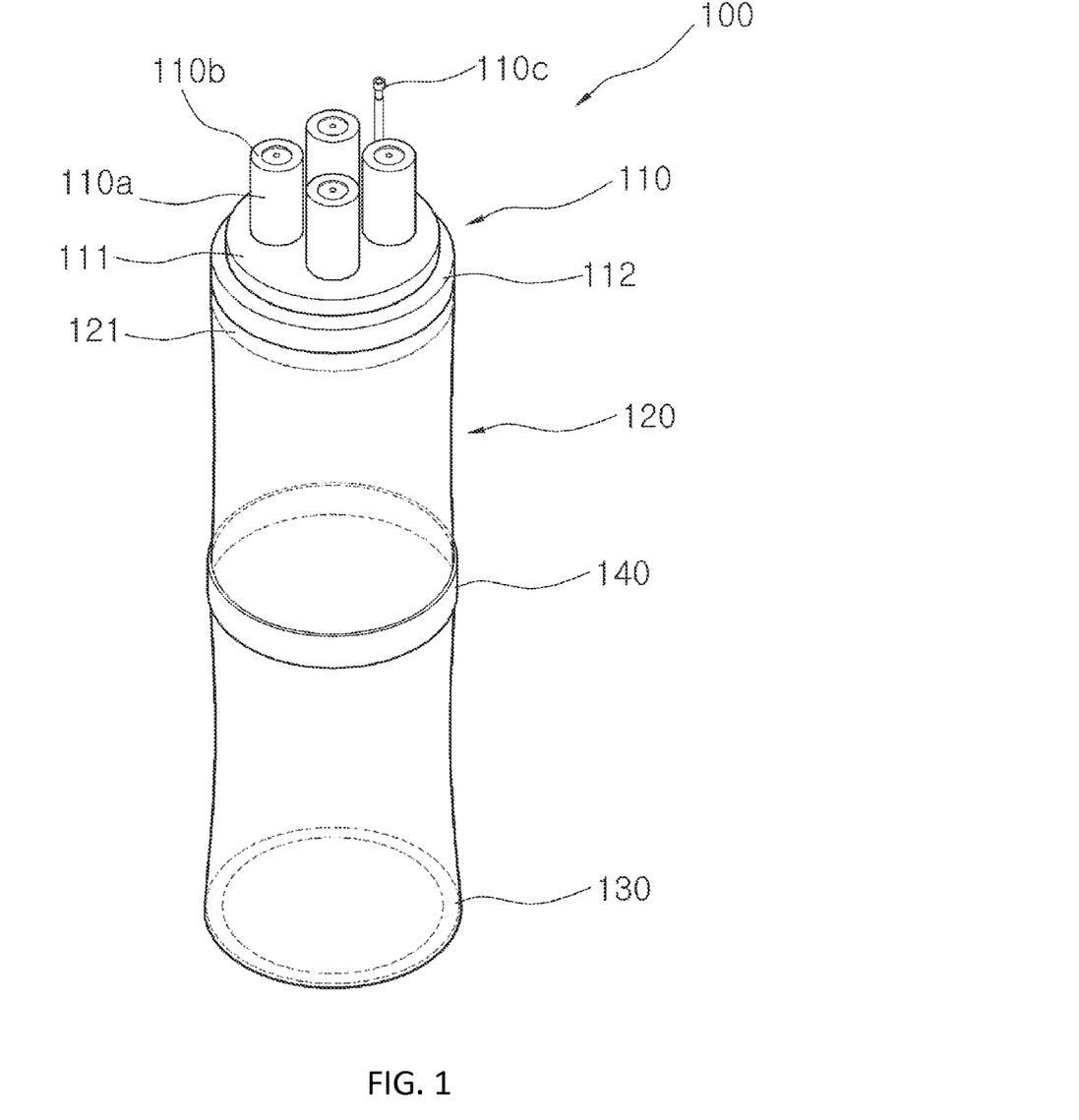
FIG. 1 is a perspective view showing an endoscopic instrument guide port according to a first embodiment of the present invention.
Figure 2:
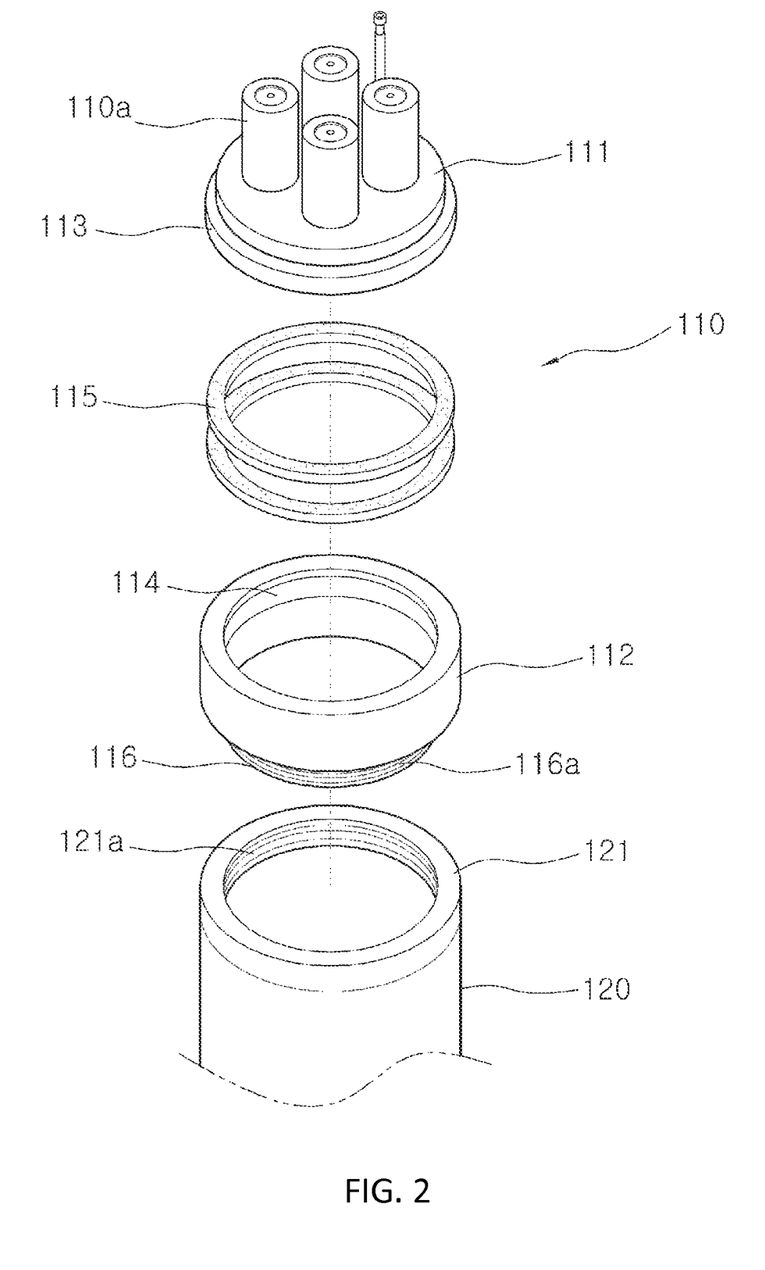
FIG. 2 is an exploded perspective view showing a main body member and a protective tube according to the first embodiment of the present invention.
Figure 3:
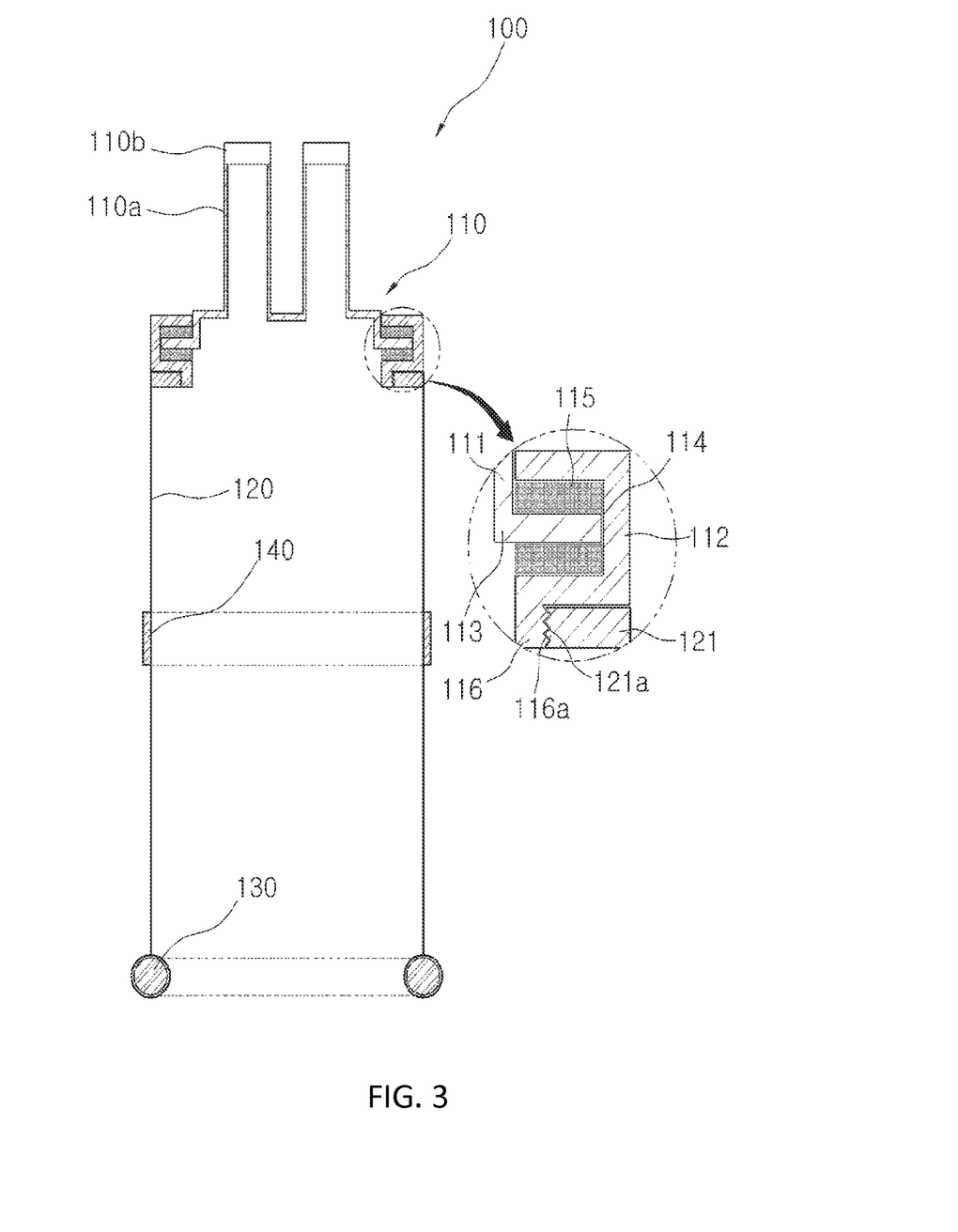
FIG. 3 is a sectional view showing an endoscopic instrument guide port according to the first embodiment of the present invention.

To this end, the main body member 110 may include an upper cap 111 and a rail ring member 112 for supporting the upper cap 111 such that the upper cap 111 can horizontally rotate.

At least one surgical instrument entrance part 110a may be formed at the top surface of the upper cap 111 and a shaft end 113 may protrude at the lower end of the upper cap 111.

A rail space portion 114 may be formed inside the rail ring member 112 such that the rail space portion 114 may receive the shaft end 113 of the upper cap 111 therein to allow the shaft end 113 to be slidably rotated in a horizontal direction.

Thus, in the state that the shaft end 113 of the upper cap 111 is received in the rail space portion 114 of the rail ring member 112, while the shaft end 113 is sliding, the shaft end 113 may be rotated in the horizontal direction, so that the upper cap 111 is rotatably supported by the rail ring member 112. Thus, the upper cap 111 may be freely rotated in the horizontal direction as necessary. Therefore, it may be understood that a position of the surgical instrument entrance part 110a which is formed in the upper cap 111 can be changed.

Meanwhile, a packing ring member 115 may be received in the rail space portion 114, such that the packing ring member 115 may be installed on and below the shaft end 113 received in the rail space portion 114.

The packing ring member 115 enhances a sealing function between the shaft end 113 and the rail space portion 114, so that efficiency to prevent the gas leakage can be improved. A silicon material packing ring may be employed as the packing ring member 115.

Further, the surgical instrument guide port 100 according to the first embodiment of the present invention may be implemented such that the main body member 110 can be separated from the protective tube 120.

To this end, a coupling ring 121 may be provided at an upper end portion of the protective tube 120, and a coupling member 116, which is detachably connected to the coupling ring 121, may be formed at a lower end portion of the rail ring member 112.

The detachable coupling scheme between the coupling ring 121 and the coupling member 116 may be variously implemented. As shown in the drawings as one example, a female screw portion 121a is formed on an inner surface of the coupling ring 121 and a male screw 116a is formed on an outer surface of the coupling member 116, so that the coupling ring 121 and the coupling member 116 may be detachably coupled to each other in a screw coupling scheme.

Figure 5:
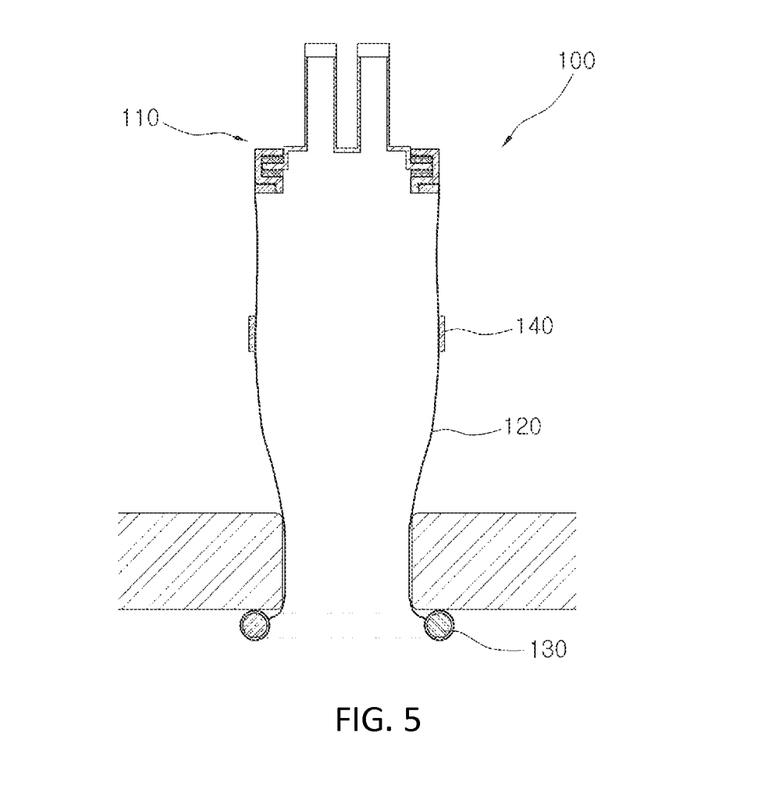
FIGS. 5 to 7 are exploded perspective views illustrating an operation of endoscopic instrument guide port according to the first embodiment of the present invention.
Figure 6:
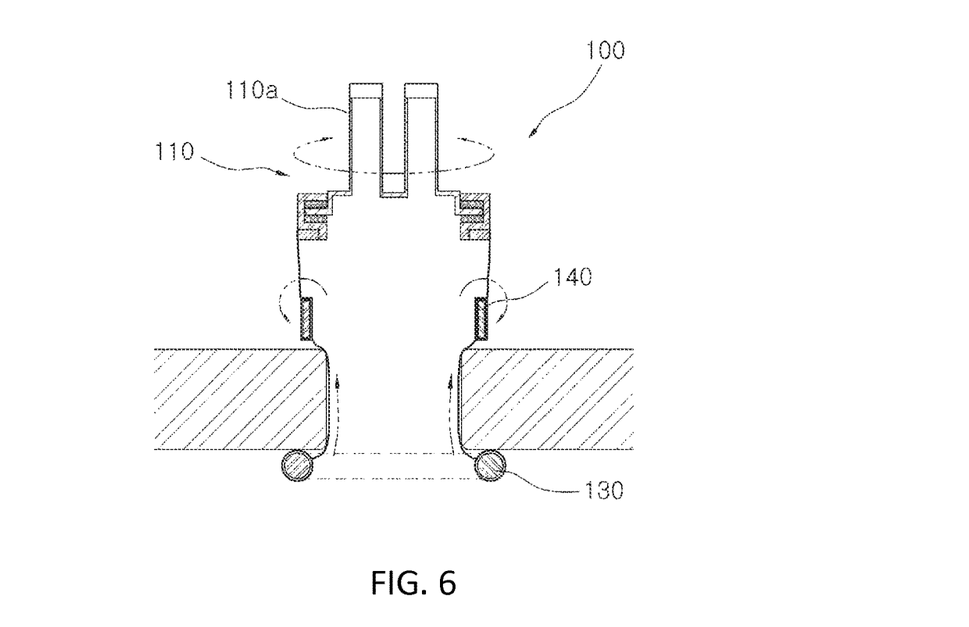
Figure 7:
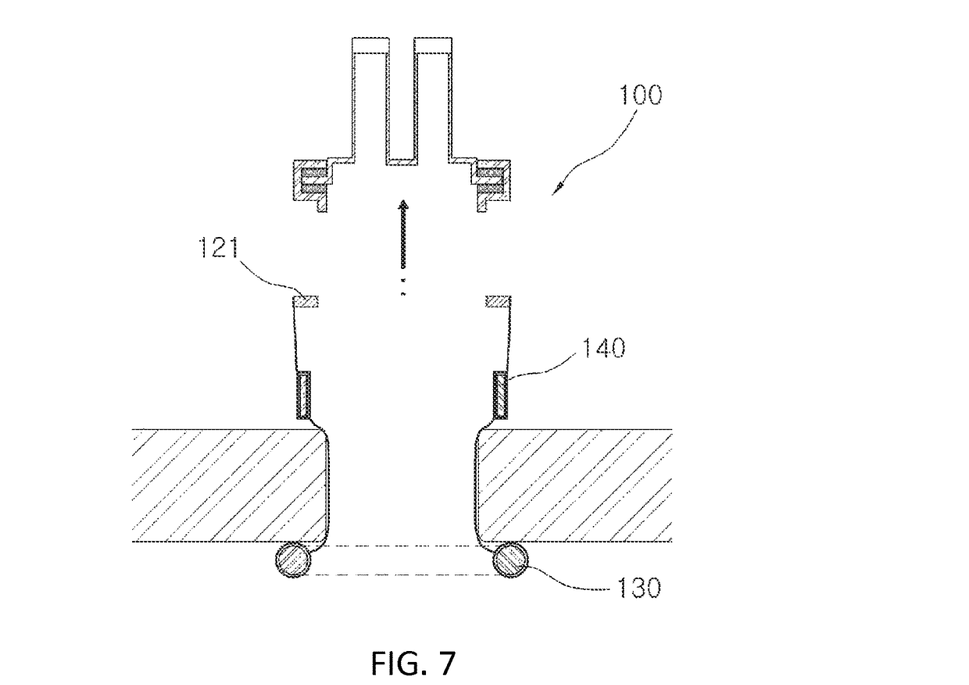

FIGS. 5 to 7 are views illustrating an installation and an operation of the surgical instrument guide port 100 according to the first embodiment of the present invention. The operation of the surgical instrument guide port 100 according to the first embodiment of the present invention will be described with reference to FIGS. 5 to 7 as follows.

First, as shown in FIG. 5, after an operation hole for a laparoscopic operation is perforated at the navel of a patient, a portion of the surgical instrument guide port 100 is introduced through the operation hole.

In more detail, after folding or shrinking the support ring member 130 fixed to a lower end portion of the protective tube 120 in a narrow size, the support ring member 130 is introduced into the abdominal cavity through the operation hole.

Then, after completely passing through the operation hole, the introduced support ring member 130 is restored to the original state (that is, the annular state) due to the resilient force thereof, and accordingly, the support ring member 130 is expanded in the belly with the restoring force and is naturally suspended to the abdominal wall.

After the surgical instrument guide port 100 is installed at the operation hole through the support ring member 130 and the gas for expanding the belly is introduced (formation of gas belly), various surgical instruments (not shown) such as an endoscopy are introduced into the belly through the surgical instrument entrance part 110a, such that an entropic operation is performed.

According to the surgical instrument guide port 100 of the present invention, before the gas for expanding the belly is introduced or while the entropic operation is being performed, as shown in FIG. 6, the length of the protective tube 120 is reduced through the folding operation of the adjustment ring member 140 so that the distance between the surgical instrument entrance part 110a and the operation hole may be reduced and the protective tube 120 is more tensioned. Thus, the space where the surgical instrument is moved may be expanded and a vision may be broadened, thereby facilitating the smooth operation.

While the entropic operation is proceeding by using the surgical instruments, if there is a need to change the positions of the surgical instruments, the positions of the surgical instruments may be changed by rotating the upper cap 111 without taking the surgical instruments out of the surgical instrument guide port 100.

In addition, when an organic extraction having a large size is removed while performing an entropic operation, the organic extraction must be taken out of the belly. In this case, as shown in FIG. 7, after the coupling member 116 of the rail ring member 112 coupled to the coupling ring 121 of the protective tube 120 is rotated in a screw releasing direction to allow the main body member 100 to be separated upward from the protective tube 120, the organic extraction may be taken out of the belly through the opened upper end portion of the protective tube 120.

As described above, according to the endoscopic instrument guide port 100 of the first embodiment of the present invention, the length adjustment of the protective tube and the traction force may be easily achieved through the adjustment ring member and the main body member may be rotated and separated, so that a suitable treatment may be performed according to an operation situation, so a delay of operation time may be prevented and endoscopic operation may be more smoothly performed.

Figure 8:
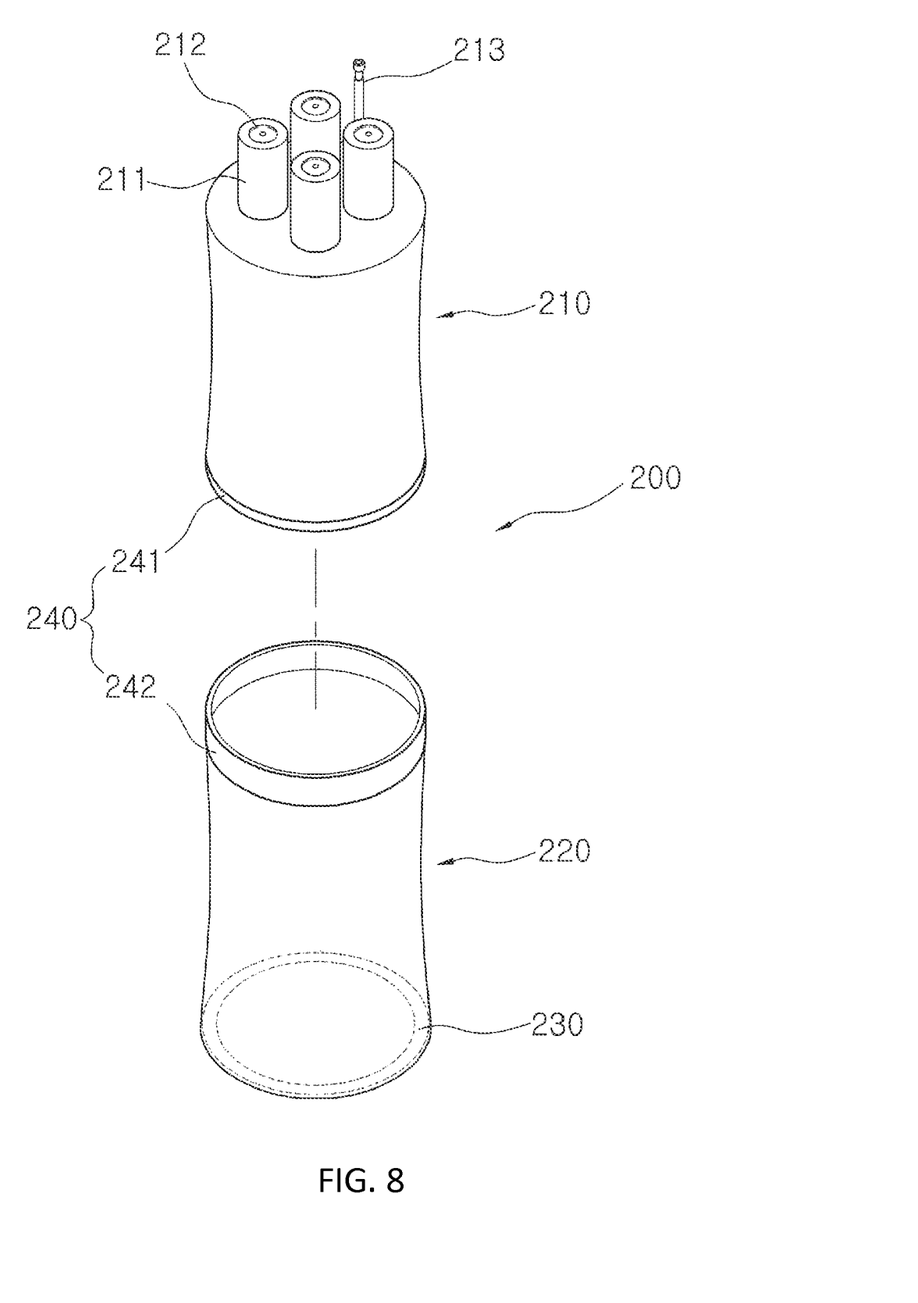
FIG. 8 is a perspective view showing an endoscopic instrument guide port according to the second embodiment of the present invention.
Figure 9:
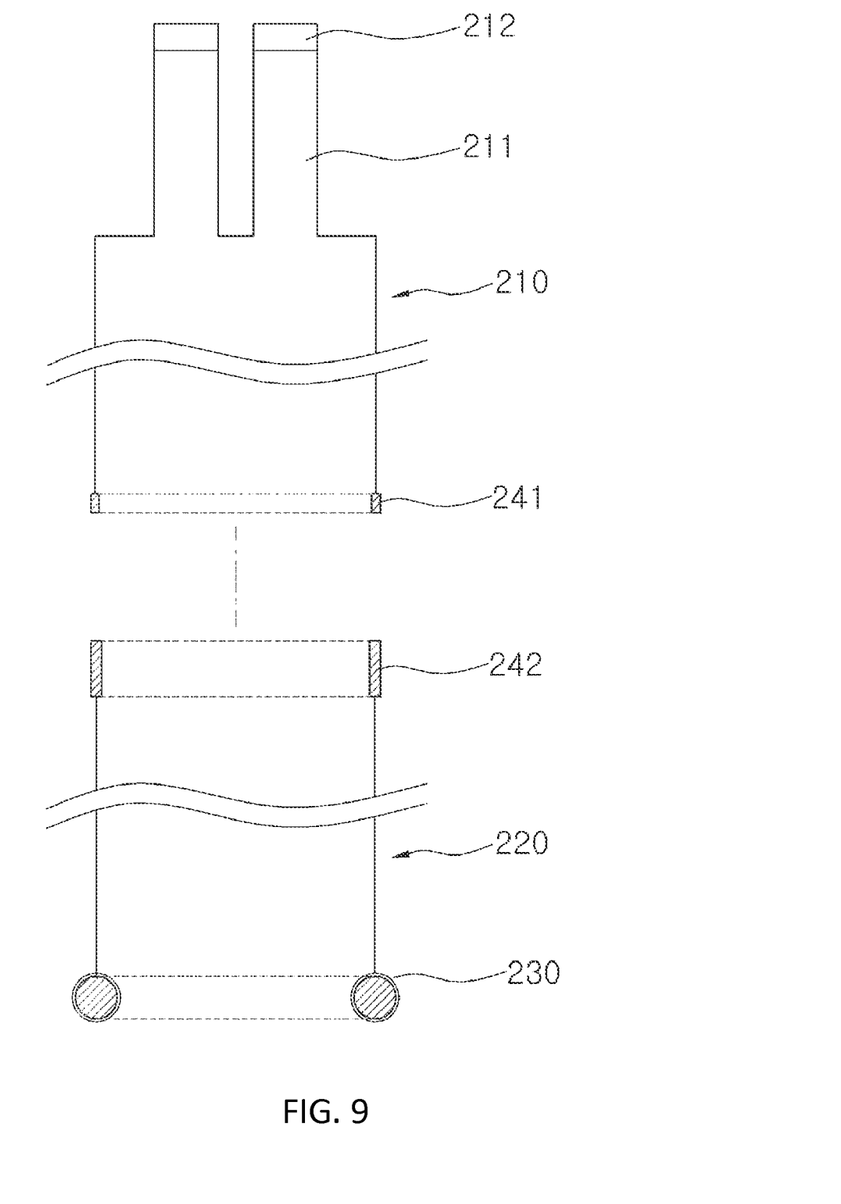
FIG. 9 is a sectional view of FIG. 8.

FIGS. 8 and 9 are perspective and sectional drawings showing an endoscopic instrument guide 200 according to the second embodiment of the present invention. Referring to the drawings, an endoscopic instrument guide port (hereinafter, referred to as 'surgical instrument guide port') 200 according to the second embodiment of the present invention includes an upper tube 210, a lower tube 220, a support ring 230 and a tube connection unit 240.

First, At least one surgical instrument entrance part 211 is formed at an upper end portion of the upper tube 210.

The surgical instrument entrance part 211 is adapted to introduce various surgical instruments for an operation into the surgical instrument guide 200, and a valve unit 212 may be provided at an upper end of the surgical instrument entrance part 211 for easily introducing the surgical instruments while preventing leakage of gas as possible. Various structures for the surgical instrument entrance part 211 are well known in the art, to which the present invention pertains, and the surgical instrument entrance part 211 may have various known structures, and the surgical instrument entrance part 211 may not be limited to those shown in the drawings.

A gas adjusting valve 213 may be provided at an upper end portion of the upper tube 210 in addition to the surgical instrument entrance part 211, and the gas adjusting valve 213 is adapted to control entry and exit of the gas for expanding a belly during an operation.

The lower tube 220 is implemented separately from the upper tube 210 and has a structure in which an upper end portion and a lower end portion are all opened. The upper tube 210 and the lower tube 220 may be formed of a urethane sheet having an excellent resiliency and durability.

The support ring 230 which is a ring having an annular shape is provided to a lower end portion of the lower tube 220. When the surgical instrument guide 200 is installed, the support ring 230 is suspended to an abdominal wall in an abdominal cavity after passing through an operation hole of a patient. Thus, the support ring 230 is formed of a resilient material which can be freely deformed, that is, can be folded or shrunk to be easily suspended during and after passing through the operation hole, and can be directly restored into an original state if an external force is removed.

The tube connection unit 240 connects the upper and lower tubes 210 and 220, which are separately formed from each other. The tube connection unit 240 may include an upper ring member 241 and a lower ring member 242.

The upper ring member 241 is fixed to a lower end portion of the upper tube 210, and the lower ring member 242 is fixed to an upper end portion of the lower tube 220 corresponding to the upper ring member 241. Similar to the support ring 230, the upper and lower ring members 241 and 242 may be formed of a resilient material.

Further, sections of the upper and lower ring members 241 and 242 may have a rectangular shape. Specifically, the section of the lower ring member 242 preferably has a rectangular shape such that the lower tube 220 is easily coiled around the lower ring member 242 while the section of the lower ring member 242 is being folded outward. In addition, as shown in the drawings, a longitudinal length of the section of the lower ring member 242 is preferably longer than that of the upper ring member 241.

Figure 10:
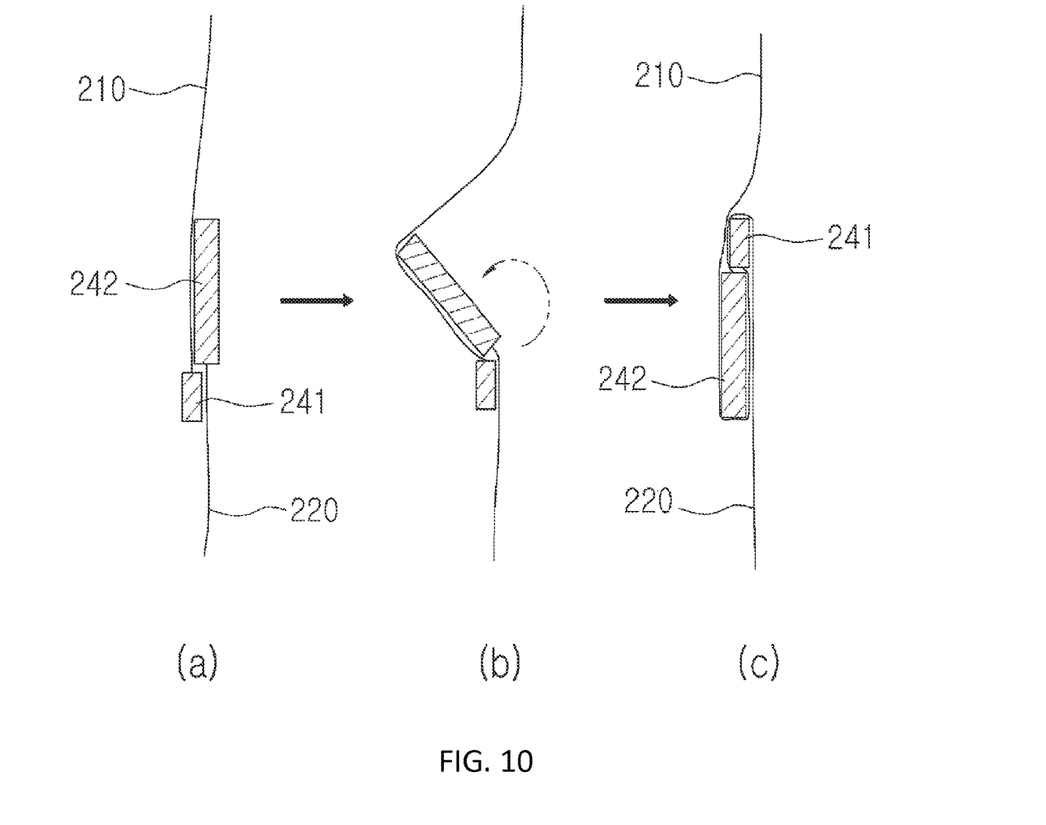
FIG. 10 is a view illustrating an operation of a tube connection unit according to the second embodiment of the present invention.

According to the tube connection unit 240, in the state of fitting the upper ring member 241 around the lower ring member 242 as shown in (a) of FIG. 10, the lower ring member 242 is folded outward as shown in (b) of FIG. 10, so that the folded upper and lower ring members 241 and 242 are coiled together as shown in (c) of FIG. 10. Thus, the separated upper and lower tubes 210 and 220 are connected to each other in a tight and sealed state. The connected upper and lower tubes 210 and 220 may be simply separated from each other by releasing the folded lower ring member 242 in an opposite direction.

Further, if the coiling number of the lower ring member 242 is adjusted, the entire length of the surgical instrument guide port 200 may be controlled. That is, in the state shown in (c) of FIG. 10, if the lower ring member 242 is continuously coiled, the lengths of the upper and lower tubes 210 and 220 are reduced while the lengths of the upper and lower tubes 210 and 220 are being reduced, so that the distance between the surgical instrument entrance part 211 and the belly may be shorten, so the operation hole may be more expanded while the tube is being more tightly strained.

Figure 11:
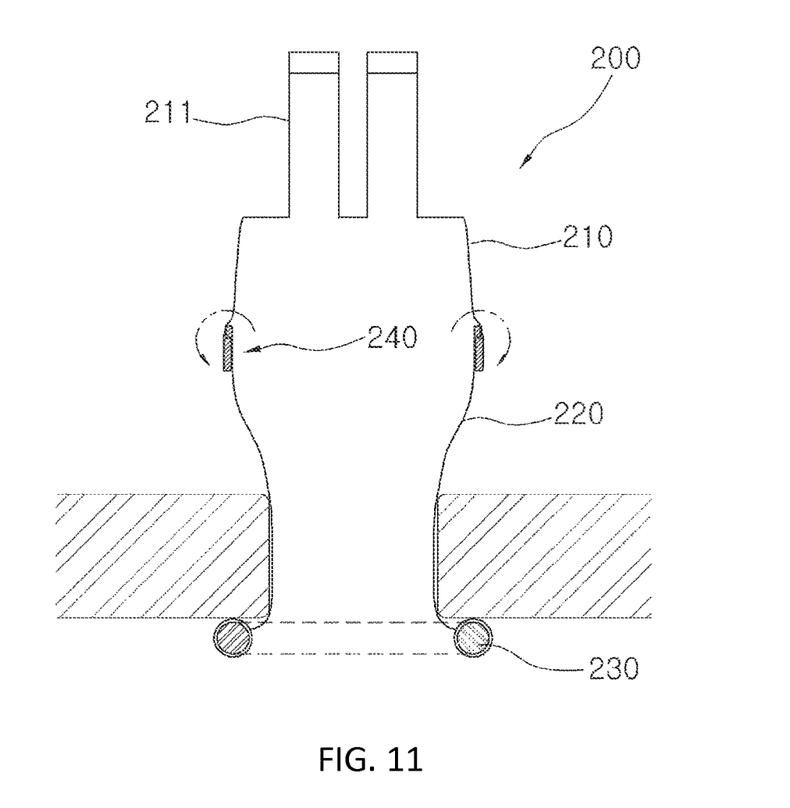
FIG. 11 is a view illustrating an installation state of an endoscopic instrument guide port according to the second embodiment of the present invention.
Figure 12:
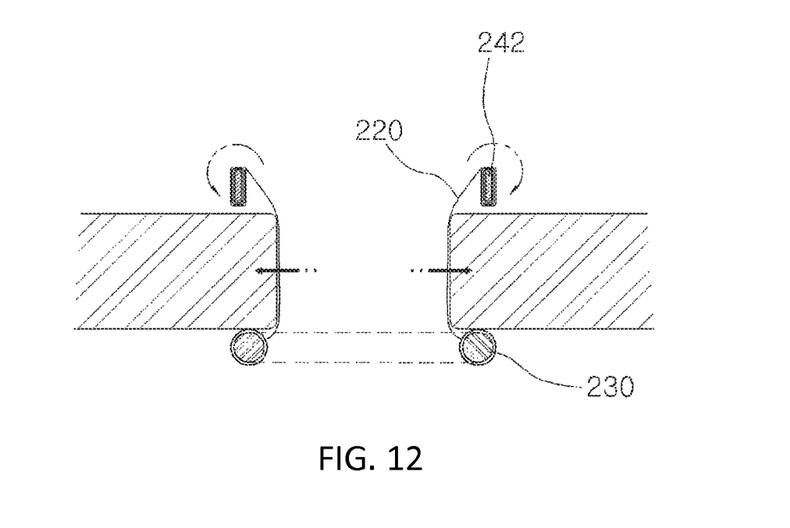
FIG. 12 is a view illustrating a separated state of an upper tube of an endoscopic instrument guide port according to the second embodiment of the present invention.

FIGS. 11 and 12 are views illustrating an installation and an operation of the surgical instrument guide port 200 according to the second embodiment of the present invention. The operation of the surgical instrument guide port 200 according to the second embodiment of the present invention will be described with reference to FIGS. 11 and 12 as follows.

First, as shown in FIG. 11, after an operation hole for a laparoscopic operation is perforated at the navel of a patient, a portion of the surgical instrument guide port 200 is introduced through the operation hole. In more detail, after the support ring 230 has been shrunk or folded to a narrow size in the state that the upper and lower tubes 210 and 220 are connected to each other through the tube connection unit 240, the support ring 230 fixed to a lower end portion of the lower tube 220 is introduced into the abdominal cavity through the operation hole.

Then, after completely passing through the operation hole, the introduced support ring 230 is restored to the original state by the resilient force thereof, and accordingly, the support ring 230 is expanded in the belly by the restoring force thereof and is naturally suspended to the abdominal wall.

As described above, if the support ring 230 is introduced and suspended to an abdominal wall, the lower ring member 242 further performs the coiling operation, so that the length of the surgical instrument guide port 200 may be properly adjusted.

In addition, after adjusting the length of the surgical instrument guide port 200, the gas for expanding the belly is introduced through the gas adjusting valve 213 provided to the upper tube 210.

Then, as the belly is expanded by the introduced gas, the upper and lower tubes 210 and 220, which are sealed and connected to each other, are expanded so that the tubes are tightly strained, so that the surgical instrument guide port 200 are stably installed in the operation hole.

As described above, if the installation of the surgical instrument guide port 200 is completed, after closing the gas adjusting valve 213, various surgical instruments (not shown) are introduced into the belly through the surgical instrument entrance part 211, such that an entropic operation is performed.

When an organic extraction is removed while a laparoscopic operation is being performed by using surgical instruments, the organic extraction must be taken out of the belly. Thus, the organic extraction may be taken out of the belly through the upper end portion of the lower tube 220 which is opened after the upper tube 210 is separated from the lower tube 220 by releasing the lower ring member 242 in an opposition direction.

Further, when the size of the organic extraction is too large to be easy to pass through the operation hole, as shown in FIG. 12, the incision portion of the operation hole is expanded by coiling only the lower tube 220 by continuously folding the lower ring member 242 in the state that the upper tube 210 is separated, so that the organic extraction may be more easily taken out.

In addition, according to the surgical instrument guide port 200 of the second embodiment of the present invention, if the upper tube 210 is separated from the surgical instrument guide port 200 and the lower tube 220 is only used as shown in FIG. 12, the lower tube 220 may be utilized as a wound protector which is used for protecting an incision portion from bacterial infection by expanding a surgical hole and preventing an incision portion from being exposed.

As described above, according to the endoscopic surgical instrument guide port 200 of the second embodiment of the present invention, a large size of an organic extraction can be easily taken out of the belly and the length of the guide port can be easily adjusted, so that an operation can be smoothly performed. In addition, besides the surgical instrument guide, the present invention can provide a wound protector by separately utilizing the lower tube.

Although exemplary embodiments of the present invention have been described until now, the scope of the present invention is not limited to the embodiments and the contents of the drawings, but the equivalent configurations corrected or modified by those skilled in the art to which the present invention pertains fall within the scope of the present invention.

The invention claimed is:

1. An endoscopy instrument guide port, comprising:
   a main body member having a top end at which at least one surgical instrument entrance part is formed;
   a protective tube extending downward from the main body member by a predetermined length;
   a support ring member provided at a lower end portion of the protective tube, the support ring member being freely deformable and restorable; and
   an adjustment ring member fixed to the protective tube at a predetermined position lengthwise along the protective tube, the protective tube configured to coil around the adjustment ring member to adjust a length of the protective tube by turning the protective tube around the adjustment ring member, the adjustment ring member fixed to the protective tube at said predetermined position before, during and after the protective tube's turning.

2. The endoscopy instrument guide port of claim 1, wherein the main body member includes:
   an upper cap having a top end at which said at least one surgical instrument entrance part is formed; and
   a rail ring member connected to the protective tube to support the upper cap such that the upper cap is able to horizontally rotate.

3. The endoscopy instrument guide port of claim 2, wherein a rail space portion is formed inside the rail ring member, and a shaft end protrudes from a lower end of the upper cap and is received in the rail space portion such that the shaft end is slidably rotated in a horizontal direction.

4. The endoscopy instrument guide port of claim 2, wherein a coupling ring member is formed at an upper end portion of the protective tube, a coupling member coupled to the coupling ring member is formed at a lower end portion of the rail ring member, and the rail ring member and the protective tube are detachably connected to each other.

5. An endoscopy instrument guide port, comprising:
   an upper cap having a top end at which at least one surgical instrument entrance part is formed;
   a rail ring member supporting the upper cap such that the upper cap is able to rotate in a horizontal direction;
   a packing ring member received in a rail space portion and disposed above and below a shaft end in the rail space portion, wherein the rail space portion is formed inside the rail ring member, and the shaft end protrudes from a lower end of the upper cap and is received in the rail space portion such that the shaft end is slidably rotated in a horizontal direction;
   a protective tube connected to the rail ring member and extending downward by a predetermined length;
   a support ring member provided at a lower end portion of the protective tube, the support ring member being freely deformable and restorable; and
   an adjustment ring member fixed to an outer surface of the protective tube, the protective tube configured to be folded around the adjustment ring member in order to adjust a length of the protective tube by turning the protective tube around the adjustment ring member.

6. The endoscopy instrument guide port of claim 5, wherein a coupling ring member is formed at an upper end portion of the protective tube, a coupling member coupled to the coupling ring member is formed at a lower end portion of the rail ring member, and the rail ring member and the protective tube are detachably connected to each other.

\* \* \* \* \*